(12) United States Patent
Maitro-Vogel et al.

(10) Patent No.: US 10,611,725 B2
(45) Date of Patent: Apr. 7, 2020

(54) BETA-NAPHTHOL ETHER SULFONATES, PROCESSES FOR PREPARING THEM AND USE THEREOF AS BRIGHTNESS IMPROVERS

(71) Applicant: BASF SE, Ludwigshafen (DE)

(72) Inventors: Sophie Maitro-Vogel, Mannheim (DE); Michael Lorenz, Ludwigshafen (DE); Tobias Urban, Bensheim (DE); Silke Annika Koehler, Mannheim (DE)

(73) Assignee: BASF SE, Ludwigshafen (DE)

( * ) Notice: Subject to any disclaimer, the term of this patent is extended or adjusted under 35 U.S.C. 154(b) by 231 days.

(21) Appl. No.: 15/575,828

(22) PCT Filed: May 18, 2016

(86) PCT No.: PCT/EP2016/061065
§ 371 (c)(1),
(2) Date: Nov. 21, 2017

(87) PCT Pub. No.: WO2016/188806
PCT Pub. Date: Dec. 1, 2016

(65) Prior Publication Data
US 2018/0118671 A1 May 3, 2018

(30) Foreign Application Priority Data

May 22, 2015 (EP) .................................... 15168931

(51) Int. Cl.
| | | |
|---|---|---|
| *C07C 309/10* | (2006.01) | |
| *C07C 303/32* | (2006.01) | |
| *C25D 3/12* | (2006.01) | |
| *C25D 3/22* | (2006.01) | |
| *C25D 3/32* | (2006.01) | |
| *C25D 3/38* | (2006.01) | |
| *C25D 3/56* | (2006.01) | |
| *C11D 1/00* | (2006.01) | |
| *C25D 3/04* | (2006.01) | |
| *C25D 3/10* | (2006.01) | |

(52) U.S. Cl.
CPC .......... *C07C 309/10* (2013.01); *C07C 303/32* (2013.01); *C11D 1/00* (2013.01); *C25D 3/04* (2013.01); *C25D 3/10* (2013.01); *C25D 3/12* (2013.01); *C25D 3/22* (2013.01); *C25D 3/32* (2013.01); *C25D 3/38* (2013.01); *C25D 3/56* (2013.01); *C25D 3/565* (2013.01)

(58) Field of Classification Search
CPC ........................... C07C 303/32; C07C 309/10
See application file for complete search history.

(56) References Cited

U.S. PATENT DOCUMENTS

| | | | |
|---|---|---|---|
| 2,115,192 A | * | 4/1938 | Bruson ................ C07C 309/10 562/42 |
| 2,989,547 A | | 6/1961 | Whyte |
| 4,734,535 A | | 3/1988 | Greif et al. |
| 4,820,388 A | | 4/1989 | Kurze et al. |

FOREIGN PATENT DOCUMENTS

| | | |
|---|---|---|
| EP | 0 026 932 A2 | 4/1981 |
| EP | 0 173 832 A2 | 3/1986 |
| EP | 0 240 871 A1 | 10/1987 |
| EP | 0 298 296 A1 | 1/1989 |
| EP | 0 514 683 A1 | 11/1992 |
| EP | 1 760 173 A2 | 3/2007 |
| JP | 60-17091 A | 1/1985 |
| WO | 2008/073956 A2 | 6/2008 |
| WO | 2012/022689 A1 | 2/2012 |

OTHER PUBLICATIONS

International Search Report dated Jul. 27, 2016, in PCT/EP2016/061065, filed May 18, 2016.

* cited by examiner

*Primary Examiner* — Ana Z Muresan
(74) *Attorney, Agent, or Firm* — Oblon, McClelland Maier & Neustadt, L.L.P.

(57) ABSTRACT

The present invention relates to beta-naphthol ether sulfonic acids or salts thereof having the general formula (I) R—O—$(AO)_n$—$CH_2$—$CH_2$—$S(O)_3M$ (I), where R, AO, n and M have the definitions stated in the claims and in the description, to mixtures thereof, to aqueous solutions and to electrolytes comprising them, to processes for preparing them and to the use of these.

15 Claims, No Drawings

BETA-NAPHTHOL ETHER SULFONATES, PROCESSES FOR PREPARING THEM AND USE THEREOF AS BRIGHTNESS IMPROVERS

The present invention relates to beta-naphthol ether sulfonic acids or salts thereof, to mixtures thereof, to aqueous solutions, and to electrolytes comprising them. The invention further relates to processes for their preparation and to the use of these.

Both alkyl ether sulfonates and aryl ether sulfonates are long-established substances which are used in electrochemical deposition of metal. They are described comprehensively in, for example, EP 0 173 832 A2, WO 2012/022689 A1 and EP 0 298 296 A1.

Thus EP 0 173 832 A2 in general form describes sulfates and sulfonates of ethoxylated beta-naphthol, proposals being made for a degree of ethoxylation of 6 to 60 ethyleneoxy units and, in the case of sulfonates, for a multiplicity of spacer compounds between the last ethyleneoxy unit and the sulfonate group. These compounds are used in acidic zinc baths, where they are said to contribute to a high cloud point, in order to allow flawless metal deposition without foaming. Brighteners recited are aromatic ketones and aromatic aldehydes, such as benzalacetone and o-chlorobenzalacetone, for example.

WO 2012/022689 A1 is concerned with electrolytes for the deposition of bronze alloys on utility items and industrial articles. These alloys are intended to serve as a substitute for nickel-containing finishing coats, allowing utility goods of this kind to be finished in drum or rack electrocoating processes, inexpensively, to give allergen-free, esthetic products. In the production of these bronze coats for the electronics industry, the solderability of the resulting coat and optionally its mechanical adhesive strength are the critical properties of the coat to be produced. It is further observed in WO 2012/022689 A1 that the appearance of the coats is less significant, for application in this sector, generally speaking, than their functionality. For the production of bronze coats on utility goods, in contrast, the decorative effect (luster and brightness) is the essential target parameter, in addition to the long durability of the resulting coat, with an appearance unchanged as far as possible. The electrolytes proposed in WO 2012/022689 A1 comprise not only alkylsulfonic acids but also ionic wetting agents in the form of salts of sulfonated or sulfated aromatic alkyl aryl ethers and also, furthermore, complexing agents and dialkyl thioether derivatives.

EP 0 298 296 A1 likewise discloses beta-naphthol derivatives as wetting agents, but in the form of polyalkylene glycol-naphthyl 3-sulfonpropyl diethers and salts thereof for electroplating. These compounds are intended in particular to serve for retaining the brightener in solution, for wetting the cathode surface, and for preventing the formation of what are called hydrogen pores, which come about when hydrogen deposits cathodically on the cathodic metal surface together with the metal undergoing deposition, such as zinc, cadmium, copper, silver and the like.

Similar compounds to those from EP 0 298 296 A1 are described in EP 1 760 173 A2 for the deposition of matt zinc coats. Deposition may take place both acidically and alkalinically.

Particularly short-chain beta-naphthol ethoxylate sulfonates are known from U.S. Pat. No. 2,115,192 A. Finally, aryl ether sulfonates are also available commercially from, for example, the company Raschig, of Ludwigshafen (DE), under the brand name RALUFON® NAPE 14-90.

In spite of the compounds already known in the prior art for electrochemical deposition, there is a need for new compounds which have improved properties in relation to this deposition, particularly in the context of brightening, and more particularly there in relation to the degree of brightness and the brightness throwing power.

It is an object of the present invention, accordingly, to provide such compounds.

This object is achieved by the provision of beta-naphthol ether sulfonic acids or salts thereof having the general formula (I)

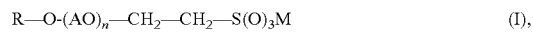

$$R\!-\!O\!-\!(AO)_n\!-\!CH_2\!-\!CH_2\!-\!S(O)_3M \qquad (I),$$

where
R is a naphth-2-yl radical which is unsubstituted or substituted by one or more radicals $R^1$;
$R^1$ is $C_{1-4}$ alkyl;
n is an integer from 3 to 25;
each AO independently of any other is selected from one of the groups $CH_2$—$CH_2$—O, $CH(CH_3)$—$CH_2$—O or $CH_2$—$CH(CH_3)$—O, and
M is H, Li, Na, K, ½ Mg, ½ Ca, ½ Sr, ½ Ba or $N(R^2)_4$, where each $R^2$ independently of any other is H, $C_{1-4}$ alkyl, phenyl or benzyl.

Surprisingly it has been found that in electrochemical deposition, such compounds are able to contribute to improved brightening properties (especially in relation to degree of brightness and brightness throwing power).

Accordingly, the compounds in question are beta-naphthol ether sulfonic acids or salts thereof in which unsubstituted or substituted beta-naphthol has undergone n-fold addition with alkoxy groups and where the last alkoxy group is followed by an ethylene group on whose other end the $SO_3M$ group is located. Where M is H, the compounds in question are the sulfonic acids. Where M is Li, Na, K, ½ Mg, ½ Ca, ½ Sr, ½ Ba or $N(R^2)_4$, the compound in question is one of the salts thereof.

For the skilled person it is obvious that for divalent metals, such as Mg, there is a formal requirement for only half of the charge of the metal for charge exchange with the anion. Accordingly, this corresponds to a formula $[R\!-\!O\!-\!(AO)_n\!-\!CH_2\!-\!CH_2\!-\!S(O)_3]_2M$ for the divalent metals Mg, Ca, Sr and Ba.

Besides the monovalent metals Li, Na, and K an ammonium salt ($M=N(R^2)_4$) is also possible. The radical $R^2$ in this case, in each case independently, is H, $C_{1-4}$ alkyl, phenyl or benzyl.

For the purposes of the present invention, "$C_{1-4}$ alkyl" is a branched or unbranched, saturated hydrocarbon chain having one to four carbon atoms. The radicals in question here are as follows: methyl, ethyl, n-propyl, isopropyl, n-butyl, sec-butyl, tert-butyl, especially methyl. The four radicals $R^2$ may be identical or different, and are preferably identical. If they are different, possible examples include methylammonium, dimethylammonium, trimethylammonium, ethylammonium, diethylammonium or methyldiethylammonium. If the radicals are identical, the species are ammonium ($NH_{4+}$) or tetramethylammonium. It is self-evident that in formula (I) the charges are not shown, since they cancel each other out. Accordingly, instead of the ammonium cation, $M=NH_4$ occurs in the formula.

In formula (I), R is a naphth-2-yl radical which may be unsubstituted or substituted by one or more radicals $R^1$. In one embodiment, accordingly, R may be unsubstituted. In another embodiment, R is substituted. The number of substituents may be 1, 2, 3, 4, 5, 6 or 7. The number of substituents is preferably 1, 2 or 3, more preferably 1. These substituents may be identical or they are different. Preferably they are identical. A preferred substituent is methyl. It is preferred, however, for R to be an unsubstituted naphth-2-yl radical.

In formula (I), n indicates the number of alkoxy groups AO. This number is in the range from 3 to 25. Accordingly there may be at least three and not more than 25 AO units present. For an individual compound, n is an integer. There may of course also be two or more compounds of the formula (I) present in the mixture. In that case there may be an average number n, which is a rational number but is nevertheless within the range from 3 to 25.

The number n is in the range from 3 to 25, preferably n is a number from 6 to 20. More preferably n is a number in the range from 8 to 15, and more particularly n is the number 11.

The alkoxy groups AO are ethylenoxy groups ($CH_2$—$CH_2$—O, EO) or propyleneoxy groups (PO) ($CH(CH_3)$—$CH_2$—O (2-PO) or $CH_2$—$CH(CH_3)$—O (1-PO)). For the skilled person it is clear that the orientation of the groups is such that the oxygen atom of the oxy group joins on in each case to a carbon atom of the next group, forming ether functionalities and not peroxy groups. In the case of propyleneoxy groups, there is a general preference for these to be formed by only one of the two isomers. In that case the isomer $CH_2$—$CH(CH_3)$—O is preferred.

The number n may be obtained as the sum of k+l, where k is the number of $CH_2$—$CH_2$—O groups and l is the number of the two groups $CH(CH_3)$—$CH_2$—O and $CH_2$—$CH(CH_3)$—O. Here, accordingly, k and l may adopt values of 0 to 25, with the sum k+l being in the range from 3 to 25. For preferred ranges of n, the same applies analogously for k and l.

Accordingly there may be different groups EO and 1-PO; EO and 2-PO; 1-PO and 2-PO; EO, 1-PO and 2-PO; or identical groups EO, 1-PO or 2-PO. In the case of the different groups, EO and 1-PO is preferred. In the case of the identical groups, EO is preferred.

Where different groups occur, they may be arranged in alternation, blockwise or at random, provided this is allowed by the number n. In the case of an alternating group, the different AO groups alternate, for example EO, 1-PO, EO, 1-PO, ..., whereas a blockwise arrangement envisages at least one AO group having at least two adjacent AO units—for example, 1-PO, 1-PO, EO. In the case of a random arrangement there is no evident pattern.

Where different AO groups are present, it is preferred if the naphthol group is followed first of all by one or two 1-PO groups and then exclusively by EO groups. It is preferred, accordingly, if l=1 or 2 and k is 1 to 23 with the stated sequence, and l+k=n, i.e. l+k=3-25. For preferred n, k should be adapted accordingly, while l=1 or 2.

In one preferred embodiment there are different AO groups, with k>0 and l>0. Accordingly, EO and PO (preferably 1-PO) groups are present. Preferably there are at least 50 mol % of EO groups present. It is further preferred for k>l. Accordingly, there are more EO groups than PO groups present, corresponding to a molar fraction of more than 50 mol % based on all AO groups. Further preferred is a fraction of at least 80 mol % of EO.

In an alternative preferred embodiment, there is only one group AO present. In this case it is preferred for AO to be exclusively EO ($CH_2$—$CH_2$—O; k=n, l=0).

As already observed at the outset, the compounds of general formula (I) are acids (M=H) or salts thereof (M=Li, Na, K, ½ Mg, ½ Ca, ½ Sr, ½ Ba or $N(R^2)_4$). On account of their water solubility, however, preference is given to the salts. More preferred in this case are the monovalent cations, and particularly preferred within that group are Na and K, especially Na.

Especially preferred is the salt of the formula:

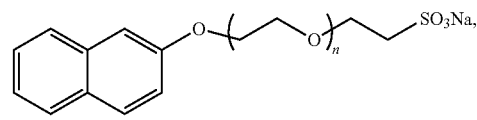

where n=11.

This salt derives from the formula (I), with R being an unsubstituted naphth-2-yl radical, n being 11, AO being EO, and M being Na.

In accordance with the invention, the compounds of the general formula (I) may be used as individual compounds or in a mixture. If there is a mixture present, the compounds may differ in the radical R, in the nature of the group AO in the case of the number n, and/or in M. Mixtures are produced in particular as a result of the preparation process, in which either mixtures are actually used or mixtures are produced during the preparation process. If a mixture is present, a particular individual compound may be obtained by known separation techniques, such as high-throughput chromatography. However, since this is expensive, the present invention uses mixtures of two or more sulfonic acids or salts thereof according to the invention. Accordingly, it is possible to use different sulfonic acids, different salts, and/or different sulfonic acids and salts.

The starting material obtained is customarily a mixture of naphthol alkoxylates having different degrees of alkoxylation. It is preferred, accordingly, if the compounds differ only in the number n of AO groups.

The present invention further provides an aqueous solution comprising a sulfonic acid salt of the invention or a salts mixture of the invention. In the context of the present invention, a solution is aqueous if only water is used as solvent or if at least more than half of all the solvents by volume are water. Where other solvents are present, they are advantageously miscible with water at room temperature and under atmospheric pressure. Generally, however, water exclusively is preferred.

Additionally provided by the present invention is an electrolyte for electrochemical metal deposition, comprising
(A) a sulfonic acid salt of the invention or a salts mixture of the invention,
(B) at least one metal salt for the deposition of the corresponding metal, and
(C) optionally at least one metal deposition component other than (A) and (B).

In the context of the present invention, the term "base electrolyte" for the electrochemical deposition of metal refers to an electrolyte without component (A).

Component (A) is formed by a sulfonic acid salt as elucidated in more detail above, corresponding to formula (I), or by a relevant mixture. It is added to the base electrolyte customarily in the form of an aqueous solution according to the invention. The electrolyte, accordingly, is likewise an aqueous solution, and so the comments already made concerning the aqueous solution according to the invention apply analogously here.

Component (B) comprises at least one metal salt for the deposition of the corresponding metal. Accordingly, there may be only one salt present, this being preferred. It is also possible for there to be two or more salts, in other words, for example, two, three or four salts, which differ in the metal cation or in the anion, or both in the cation and in the anion.

Suitable metal salts which serve as a source for metal deposition in the metal deposition context are familiar to the skilled person. Since they are present in dissolved form in the electrolyte, the choice of the anion depends merely on ensuring the solubility of the salt and the absence of any adverse effect by the anion on the electrochemical deposition during said deposition. The choice of metal salt may also be dependent on the pH that is used. The metal salt preferably comprises a common metal salt which can be deposited by aqueous electrochemical deposition, more particularly metal salts of the metals zinc, tin, copper, nickel, chromium, or mixtures of such salts, more particularly a zinc salt, such as zinc chloride, for example; accordingly, the electrolyte, for example, has zinc ions and chloride ions, among others. The metal to be deposited, accordingly, is preferably zinc, tin, copper, nickel, chromium or alloys thereof, more particularly zinc.

Component (C) comprises at least one metal deposition substance different from (A) and (B), more particularly customary additives, especially organic additives. Such additives are known to the skilled person. Component (C) is present or not present. If it is present, it may comprise one or more, such as two, three or four, additives. Such additives for electrochemical metal deposition are known to the skilled person. Metal deposition is described for example in M. Schlesinger, M. Paunovic (Ed.), Modern Electroplating, John Wiley & Sons, Inc., Hoboken, N.J. (US), 2010. The deposition of zinc is addressed in particular in chapter 10.

Examples of typical additives are nonionic surfactants such as, for example, alkyl ethoxylates such as C10 oxo-process alcohol+11 EO, dispersants such as naphthalenesulfonic acid condensation product, Na salt for example, such as Tamol, and/or brighteners, such as benzalacetone and sodium benzoate, for example. Among the brighteners, a distinction may be made between those which are used as primary brighteners and those which serve as carriers for the wetting and contribute to the solubilization of the primary brighteners. Examples of such carriers are polyalcohols, polyamines, fatty alcohols, polyglycol ethers, and quaternary ammonium compounds. Typical primary brighteners are aliphatic, aromatic or heterocyclic carbonyl compounds.

For the purposes of the present invention, both types of brighteners are referred to collectively, for simplicity, as "brighteners".

Furthermore, typical constituents of components (C) that may be used are, for example, conductive salts such as potassium chloride and buffers such as boric acid.

The pH of the electrolyte of the invention is within the acidic range, as a result of the addition of acids, for example. This range is preferably set such that the range is from 4 to 6.5, preferably a range from 5 to 6. Acidic deposition is preferred, accordingly.

The electrolyte of the invention is heated preferably in a range from 20° C. to 40° C., preferably around 23° C. The range from 15° C. to 55° C. is also possible, however. It is possible to set a current density which is in the range from 0.01 ampere per square decimeter [A/dm2] to 15 A/dm2, and which is dependent on the nature of the coating unit. The cell voltage may also vary, customarily from 1 to 12 V.

A further subject of the present invention is a process for preparing a sulfonic acid of the invention or salt thereof, comprising the steps of:
(a) reacting a compound of the formula R—O-(AO)$_{n+1}$—H with phosgene to give a compound R—O-(AO)$_n$—CH$_2$—CH$_2$—Cl and (b) reacting the compound R—O-(AO)$_n$—CH$_2$—CH$_2$—Cl with MHSO$_3$ to give a compound of the general formula (I), the variables R, AO, n, and M being indicated above.

A typical exemplary preparation process in a continuous reactor via the two-stage operation described above is indicated using the reaction equation below, where Cyanex is a commercial catalyst:

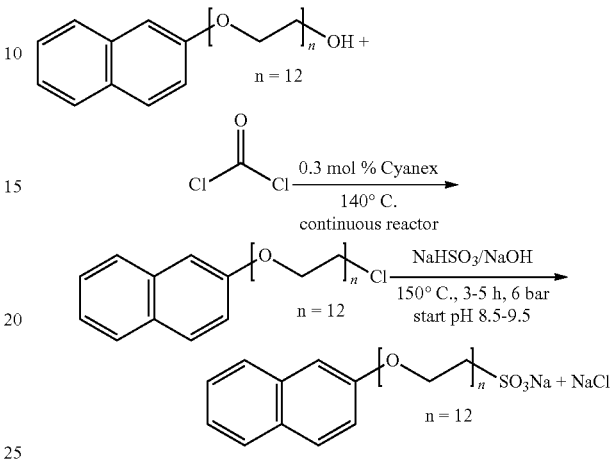

The conversion of polyether alcohols generally into the corresponding chlorides through a reaction with phosgene is described in, for example, EP 0 514 683 A1 and EP 0 240 871 A1.

This type of reaction (step (a)) may be operated either batchwise or continuously. The reaction is customarily carried out under atmospheric pressure, but may also be carried out in pressure apparatus for phosgenations. For the reaction it is possible to use the catalysts described in EP 0 514 683 A1 and EP 0 240 871 A1, namely aliphatic, cycloaliphatic or cyclic/aliphatic phosphine oxides or alkylammonium chlorides. The amount of catalyst may be limited at the bottom end down to 0.075 mol % in respect of alcohol; at the top end, the only limits are those imposed by economics. A catalyst is very advantageous, since otherwise a chloroformate may be formed, and may in turn be converted into the corresponding chloride. This reaction, however, is very time-consuming and leads to a significantly greater number of byproducts. The metering rate of the alcohol is determined by the reaction rate in the reaction. Excessively rapid metering leads to an uncontrollable evolution of heat and to the formation of byproducts. The temperature range is preferably from 20° C. to 180° C. However, the choice of temperatures as low as possible is advantageous. The required temperature has a direct influence on the excess of phosgene, since the low boiling point of phosgene means that large amounts thereof limit the reaction temperature at the upper end. It is useful to use an excess of phosgene (1.01-10 eq. in respect of alcohol). The excess is rationally to be as small as possible. The reaction procedure is advantageously such that a gentle reflux of phosgene is in evidence. The reaction can be carried out in solution or in bulk, preferably in bulk. Solvents used may be all common phosgenation solvents, such as chlorobenzene, dichlorobenzene, toluene, benzene, THF, dichloromethane, etc.

A product of the reaction in step (a) is a chloride of the formula R—O-(AO)$_n$—CH$_2$—CH$_2$—Cl, where R, AO and n have the general or preferred definition indicated above. This chloride is reacted further in step (b).

Step (b) is a suffonation with sulfite. Accordingly, the compound R—O-(AO)$_n$—CH$_2$—CH$_2$—Cl reacts with MHSO₃ to give a compound of the general formula (I), with the variables R, AO, n and M having the definition indicated above.

The sulfonation in step (b) using sulfite is also general knowledge. Reference may be made here, for example, to EP 0 026 932 A2 and U.S. Pat. No. 2,989,547 A. The sulfonation takes place preferably in the presence of iodide salts in a Finkelstein reaction (WO 2008/073956 A2). The sulfite, more particularly sodium sulfite, is used preferably in aquimolar quantities or in excess in relation to the chloride reactant. Preference is given to an excess, more particularly a molar excess of 0.01 to 0.1 mol %, in respect of the reactant.

The sulfonation in step (b) is carried out preferably at a temperature in the range from 130° C. to 180° C. The pH is preferably 8 to 10. The pH may be controlled where appropriate by the addition of the sulfite.

Both alkyl ether sulfonates and aryl ether sulfonates are long-established substances which are used in electrochemical deposition of metal. They are described comprehensively in, for example, EP 0 173 832 A2, WO 20121022689 A1 and EP 0 298 296 A1.

These substances, in the context of electrochemical deposition of metals, generally fulfill three functions:
1. Wetting of the surface: resulting in better deposition and adhesion of the deposited metal coat.
2. Solubilization of the secondary brighteners: as pure substances, these are not soluble in the aqueous media (in the case of acidic Zn depositions, for example, the substance in question may be benzalacetone).
3. Raising of the cloud point CP: as well as anionic surfactants there are also nonionic surfactants and products of electrochemical degradation in the electroplating baths, and these may lower the CP.

Furthermore, the aryl ether sulfonates specifically fulfill a further purpose. On account of their aromatic fraction, they have the advantage, in addition to the properties described above, that they act as primary brighteners. That is, they also influence crystal growth and so make a partial contribution to a bright surface.

A further subject of the present invention, accordingly, is the use of a sulfonic acid salt of the invention or a salts mixture of the invention in the electrochemical deposition of metal, especially the acidic deposition. The metal is preferably zinc, tin, copper, nickel, chromium or alloys thereof, more particularly zinc.

The sulfonic acid salts of the invention or mixtures thereof according to the invention may be used directly or indirectly (or primary brighteners and carriers) as brightness improvers. Direct in the present context means that they themselves act as brighteners. Indirect in the present context means that these additives serve to increase the brightening produced by brighteners.

Accordingly, a further subject relates to the use of a sulfonic acid salt of the invention or a salts mixture of the invention as brightness improvers. They may serve to raise the cloud point, the brightness throwing power and/or the degree of brightness.

EXAMPLES

1) Reaction of Beta-Naphthol Ethoxylate (12 EO Units) with Phosgene to Give the Corresponding Chloride

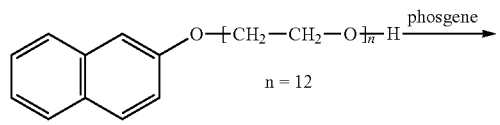

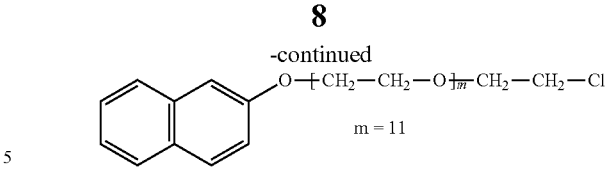

Experimental Description, Batch:

A stirred apparatus with baffles, reflux condenser with dry-ice cooling, brine cooler, thermometer, gas introduction tube, inert gas blanketing and heated dropping funnel is charged with 0.93 g of a commercially available phosphine oxide catalyst (mixture of 4 trialkylphosphine oxides, namely R₃PO, R₂R'PO, RR'₂PO, R'₃PO (R=n-octyl, R'=n-hexyl) and the stirrer is switched on. The brine cooler is set to −30° C. and the reflux condenser is charged with acetone and dry ice, and the reactor is heated to 140° C. When the reaction temperature has been reached, 25 g of phosgene are metered in and a reflux of phosgene was observed. The metered introduction of a mixture of in total 3417.5 g of beta-naphthol ethoxylate (12 EO) and 4.57 g of the aforementioned phosphine oxide catalyst was commenced. Evolution of gas is apparent. The reactants were metered in at a rate such that there was always phosgene reflux and gas evolution observable. The temperature remains at a constant 140° C. When all of the beta-naphthol ethoxylate had been added, reaction was continued at 140° C. for 1 h, followed by stripping to a phosgene-free state at 70° C. for 22 h.

Analyses carried out were ¹H and ¹³C NMR, HPLC, OH number, and determination of phosphorus. All of the analyses show complete conversion to the chloride.

Experimental Description, Continuous:

The synthesis unit consists of a reactor cascade of 2×1 L miniplant reactors made from glass, with impeller stirrer and baffles, which run continuously into one another via membrane pumps with level control (to 400 ml). Desalinated beta-naphthol ethoxylate (12 EO) and the aforementioned phosphine oxide catalyst were mixed beforehand and metered into the main reactor from a heated reservoir by means of an internally heated membrane pump. Monitoring was accomplished using a balance. The reactors were initially each equipped with a −30/−78° C. condenser pair. Adjoining this was a continuous facility for dephosgenation by stripping with nitrogen (about 150 L/h) in a heated bubble tray column (70° C.). The phosgene expelled in this facility was condensed and returned to the main reactor.

The plant was operated with 130 g/h of a mixture of beta-naphthol ethoxylate (12 EO) and the aforementioned phosphine oxide catalyst at 0.3 mol % and 13 g/h of phosgene over a total of 30 h. After this reaction time, the plant was at equilibrium; samples were taken from the two reactors and the stripping column at regular intervals, approximately every 6 h. Analyses carried out were ¹H and ¹³C NMR and HPLC, and additionally OH number and phosphorus for selected samples.

2a) Reaction of the Chloride with Na Sulfite to Give the Corresponding Sodium Beta-Naphthol Polyethoxy(11)Sulfonate (Compound 1)

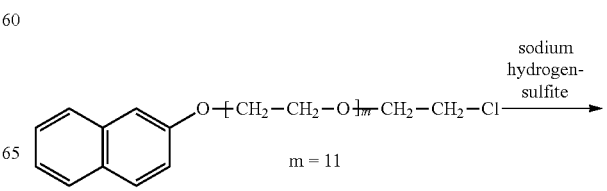

-continued

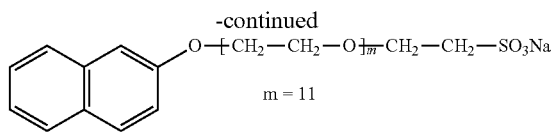

m = 11

The above-prepared chloride (1 mol) is admixed with 40% strength sodium hydrogensulfite solution (1.1 mol), and sodium beta-naphthol polyethoxy(11)sulfonate (2 wt % as aqueous solution) and potassium iodide (0.05 mol) are added. The reaction solution is adjusted to a pH of 8.5 using aqueous 10% strength NaOH solution, and then degassed with argon for 2 h with stirring. The two-phase reaction solution is transferred to a steel enamel autoclave or Hastelloy autoclave, heated to 140° C. over the course of 3 h, and maintained at that temperature for 10 h. It is then cooled, to give a homogeneous, clear and brownish reaction effluent. The pH of the product is 5.5 to 6.5.

Analyses carried out were $^1$H and $^{13}$C NMR and OH number. Complete conversion of the chloride is found, to 18% beta-naphthol ethoxylate (12 EO) and 82% sodium beta-naphthol polyethoxy(11)sulfonate.

2b) Reaction of the Chloride with Na Sulfite to Give the Corresponding Sodium Beta-Naphthol Polyethoxy(11)Sulfonate (Compound 2)

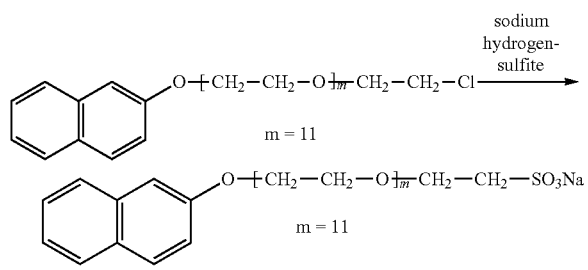

The above-prepared chloride (1 mol) is admixed with 40% strength sodium hydrogensulfite solution (1.1 mol), and sodium beta-naphthol polyethoxy(11)sulfonate (2 wt %) are added. The reaction solution is adjusted to a pH of 8.5 using aqueous 10% strength NaOH solution, and then degassed with argon for 2 h with stirring. The two-phase reaction solution is transferred to a steel enamel autoclave or Hastelloy autoclave, heated to 140° C. over the course of 3 h, and maintained at that temperature for 15 h. It is then cooled, to give a homogeneous, clear and brownish reaction effluent. The pH of the product is 6.3.

Analyses carried out were $^1$H and $^{13}$C NMR and OH number. Complete conversion of the chloride is found, to 22% beta-naphthol ethoxylate (12 EO) and 78% sodium beta-naphthol polyethoxy(11)sulfonate.

Comparative Experiments:
C1: beta-naphthol-$(PO)_{2.5}(EO)_{14}(CH_2)_3SO_3K$ (comparative compound 1) in analogy to example 6 from EP 0 298 296 A1
V2: beta-naphthol ethoxylate (12 EO units) reacted with 1,3-propane sultone (comparative compound 2) in analogy to C1, but without PO and with the corresponding amount of EO:

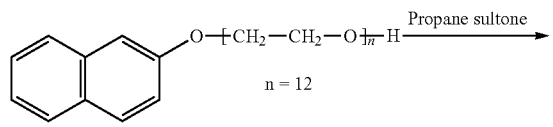

-continued

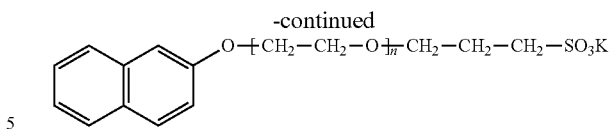

Lugalvan® BNO12+1.08 eq KOH flakes (88% form)+1 eq propane sultone, aqueous solution.
Amount: 100 g.
Active content: about 77%, remainder: NIO.
KF water determination: 6.4%

Application:
Test Method 1 (Brightness Throwing Power):

On a standard basis, additives for electrochemical deposition of metal are investigated in accordance with DIN 50957 (January 1978) in the Hull cell with a defined volume of 250 ml. Here, the left-hand side of the test substrate represents the high current density range (CDR), the right-hand side the low CDR. This method is known to the skilled person and requires no further elucidation.

Substrates used were steel plates with dimensions of 10×7 cm. These plates were subjected to alkaline degreasing, and to HCl pickling and then installed in the Hull cell. After coating, the plates were rinsed with water and dried in a stream of air.

In order to investigate the effect of the new sodium beta-naphthol polyethoxy(11)sulfonate (AES), a base electrolyte was used, for which only the AES, at different concentrations, was added and comparison was carried out.

All of the deposition tests below in the Hull cell were carried out at room temperature with a cell current of 1 A and a deposition time of 10 min.

The base electrolyte selected was the following composition in water:
73 g/L ZnCl2
275 g/L KCl
25 g/L H3BO3
2 g/L sodium benzoate,
2 g/L naphthalenesulfonic acid condensation product, Na salt
1 g/L, C10 oxo-process alcohol+11 EO
1 g/l thiodiglycol (ethoxylated)
0.2 g/L benzalacetone Added to the base electrolyte are x g/L test substance (calculated on 100%).

Application Examples

Below, the compounds of the invention were added at various concentrations to the above-described base electrolyte. For comparison, two products likewise constituting aryl ether sulfonates (AES) but having a —CH$_2$CH$_2$CH$_2$SO$_3$K end group were tested.

From the electrolyte described above, Zn is deposited in the Hull cell and the deposition picture of the zinc coat on the test substrate is evaluated for degree of brightness. Evaluation takes place of the extent of the regions on the plate that exhibits sufficient brightness, semi-brightness or a matt surface. The plate length overall is 10 cm.

3 different concentrations were measured:
AES 1 g/l=underdosing
AES 3 g/l=target concentration
AES 10 g/l=overdosing
Amount used in electrolyte 3 g/l active substance (=target concentration)

Compilation of Data:
Gloss Regions at Target Concentration (3 g/l) were Measured from the Left-Hand Edge of the Plate

|  | Compound 1 | Compound 2 | Comparative compound 1 | Comparative compound 2 |
|---|---|---|---|---|
| Matt region | 0-1.0 cm | 0-1.5 cm | 0-2.5 cm | 0-2 cm |
| Semi-bright | 1.0-3.5 cm | 1.5-2 cm | 2.5-4.5 cm | 2-4.5 cm |
| Bright | 3.5-10 cm | 2-10 cm | 4.5-10 cm | 4.5-10 cm |

Surprisingly it was found that inventive compounds in comparison to the comparative compounds, at the same use concentration, produce a significantly greater bright region on the test substrate.

This is an advantage for the coating of products in production, since it allows parts with complex shaping to be coated more uniformly.

Bright Regions at Underconcentration (1 g/l), Measured from the Left-Hand Edge of the Plate

|  | Compound 1 | Comparative compound 1 | Comparative compound 2 |
|---|---|---|---|
| Matt region | 0-0.8 cm | 0-1.0 cm | 0-1.5 cm |
| Semi-bright | 0.8-3.0 cm | 1.0-4.0 cm | 1.5-4.5 cm |
| Bright | 3.0-10 cm | 4.0-10 cm | 4.5-10 cm |

Bright Regions at Overconcentration (10 g/l), Measured from the Left-Hand Edge of the Plate

|  | Compound 1 | Comparative compound 1 | Comparative compound 2 |
|---|---|---|---|
| Matt region | 0-2.0 cm | 0-3.5 cm | 0-2.0 cm |
| Semi-bright | 2.0-3.5 cm | 3.5-6.0 cm | 2.0-3.5 cm |
| Bright | 3.5-10 cm | 6.0-10 cm | 3.5-10 cm |

Test method 2 (determination of degree of brightness):

It is also possible to determine the degree of brightness using the following instrument: Dr Lange, REFO 3, reflectometer (QM instrument No. G57, ESA/EK, type No.: LMG136, instrument No.: 1012327) at a measuring angle of 85°. The degree of brightness is determined on a steel plate galvanized with the above-described additive formulations comprising beta-naphthol ether sulfonates. The measurement was carried out according to the operating instructions of the REFO 3 instrument, starting at a distance in each case of 1 cm, 5 cm and 9 cm from the edge, and in the high current density range (hi range; see DIN 50957, January 1987). The degree of brightness found is the average value from 10 measurements. The standard deviation is ±2 degrees of brightness. The higher the degree of brightness, the greater the brightness.

| Specimen | Compound 1 | Comparative compound 1 | Comparative compound 2 |
|---|---|---|---|
| Degree of brightness [85°] | Measurement point from left-hand edge in the hI range: 1 cm/5 cm/9 cm | Measurement point from left-hand edge in the hI range: 1 cm/5 cm/9 cm | Measurement point from left-hand edge in the hI range: 1 cm/5 cm/9 cm |
| Zn on steel plate, 1 g/l | 95/145/116 | 75/142/111 | 87/144/121 |
| Zn on steel plate, 3 g/l | 85/142/118 | 33/110/114 | 51/138/115 |
| Zn on steel plate, 10 g/l | 26/121/120 | 16/64/109 | 17/112/116 |
| Zn on steel plate, basic electrolyte without additives | 45/52/57 | 45/52/57 | 45/52/57 |

It is clear that the degree of brightness at 1 cm and 5 cm is better for the inventive compound at all concentrations employed. At 9 cm, the surface becomes matt for all of the products tested, and the degree of brightness goes down and is similar for all products.

The invention claimed is:

1. A beta-naphthol ether sulfonic acid or salt thereof having the formula (I)

$$R-O-(AO)n-CH_2-CH_2S(O)_3M \qquad (I),$$

where
R is a naphth-2-yl radical which is unsubstituted or substituted by one or more radicals $R^1$;
$R^1$ is $C_{1-4}$ alkyl;
n is an integer from 3 to 25;
each AO independently of any other is selected from the group consisting of $CH_2-CH_2O$, $CH(CH_3)-CH_2-O$ and $CH_2-CH(CH_3)-O$, and
M is H, Li, Na, K, ½Mg, ½Ca, ½Sr, ½Ba or $N(R^2)_4$, where each $R^2$ independently of any other is H, $C_{1-4}$ alkyl, phenyl or benzyl.

2. The sulfonic acid or salt thereof according to claim 1, wherein R is an unsubstituted naphth-2-yl radical.

3. The sulfonic acid or salt thereof according to claim 1, wherein n is an integer from 6 to 20.

4. The sulfonic acid or salt thereof according to claim 1, wherein n is the sum of k+l, where k is the number of $CH_2-CH_2-O$ groups and l is the number of both groups $CH(CH_3)-CH_2-O$ and $CH_2-CH(CH_3)-O$, and where k>0 and l>0.

5. The sulfonic acid or salt thereof according to claim 4, wherein k>l.

6. The sulfonic acid or salt thereof according to claim 1, wherein AO is exclusively $CH_2-CH_2-O$.

7. The sulfonic acid or salt thereof according to claim 1, wherein M is Na or K.

8. A salt of a sulfonic acid according to claim 1, of the formula:

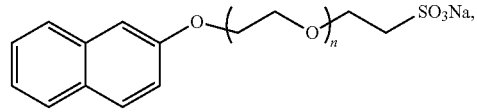

where n=11.

9. A mixture of a plurality of sulfonic acids or salts thereof according to claim 1.

10. The mixture according to claim 9, the sulfonic acids or salts thereof differing only in the number n of AO groups.

11. An aqueous solution comprising a salt of the sulfonic acid according to claim 1, or a mixture of salts thereof.

12. An electrolyte, comprising
(A) a sulfonic acid salt according to claim 1,
(B) at least one metal salt, and
(C) optionally at least one metal deposition component other than (A) and (B).

13. A process for preparing a sulfonic acid or salt thereof according to claim 1, comprising:
- (a) reacting a compound of the formula R—O-$(AO)_{n+1}$—H with phosgene to give a compound R—O-$(AO)_n$—$CH_2$—$CH_2$—Cl, and
- (b) reacting the compound R—O-$(AO)_n$—$CH_2$—$CH_2$—Cl with $MHSO_3$ to give a compound of the formula (I).

14. A method of using a salt of sulfonic acid according to claim 1, or a mixture of salts thereof in electrochemical deposition of metal.

15. A method of using a salt of sulfonic acid according to claim 1 or a mixture of salts thereof as a brightness improver.

* * * * *

UNITED STATES PATENT AND TRADEMARK OFFICE
CERTIFICATE OF CORRECTION

PATENT NO. : 10,611,725 B2
APPLICATION NO. : 15/575828
DATED : April 7, 2020
INVENTOR(S) : Sophie Maitro-Vogel et al.

It is certified that error appears in the above-identified patent and that said Letters Patent is hereby corrected as shown below:

In the Specification

Column 6, Line 66, "suffonation" should read -- sulfonation --.

Column 7, Line 9, "aquimolar" should read -- equimolar --.

Column 10, Line 44, "1 g/I" should read -- 1 g/L --.

In the Claims

Column 12, Line 63, Claim 12, "electrolyte," should read -- electrolyte --.

Signed and Sealed this
First Day of September, 2020

Andrei Iancu
*Director of the United States Patent and Trademark Office*